US007351832B2

(12) United States Patent
Giles et al.

(10) Patent No.: US 7,351,832 B2
(45) Date of Patent: *Apr. 1, 2008

(54) PROCESS FOR THE PREPARATION OF THIAZOLIDINEDIONE DERIVATIVES

(75) Inventors: Robert Gordon Giles, Tonbridge (GB); Norman John Lewis, Tunbridge Wells (GB); John Kirby Quick, Crowborough (GB)

(73) Assignee: SmithKline Beecham p.l.c., Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/550,506

(22) Filed: Oct. 18, 2006

(65) Prior Publication Data

US 2007/0066662 A1   Mar. 22, 2007

Related U.S. Application Data

(60) Continuation of application No. 11/326,003, filed on Jan. 5, 2006, now abandoned, which is a division of application No. 10/288,072, filed on Nov. 4, 2002, now Pat. No. 7,091,359, which is a continuation of application No. 10/082,995, filed on Feb. 26, 2002, now abandoned, which is a continuation of application No. 09/530,888, filed as application No. PCT/EP98/06997 on Oct. 27, 1998, now abandoned.

(30) Foreign Application Priority Data

Nov. 4, 1997   (GB)   ................... 9723295.3

(51) Int. Cl.
C07D 417/12   (2006.01)
(52) U.S. Cl. .................................. 546/269.7
(58) Field of Classification Search .............. 546/269.7
See application file for complete search history.

(56) References Cited

U.S. PATENT DOCUMENTS

| 4,725,610 | A | 2/1988 | Meguro et al. |
| 5,002,953 | A | 3/1991 | Hindley |
| 5,194,443 | A | 3/1993 | Hindley |
| 5,232,925 | A | 8/1993 | Hindley |
| 5,260,445 | A | 11/1993 | Hindley |
| 5,521,201 | A | 5/1996 | Hindley et al. |
| 5,646,169 | A | 7/1997 | Hindley et al. |
| 5,726,055 | A | 3/1998 | Hindley et al. |
| 5,741,803 | A | 4/1998 | Pool et al. |
| 5,756,525 | A | 5/1998 | Hindley et al. |
| 5,910,592 | A | 6/1999 | Pool et al. |
| 6,288,095 | B1 | 9/2001 | Hindley et al. |
| 6,632,947 | B2 | 10/2003 | Giles et al. |

(Continued)

FOREIGN PATENT DOCUMENTS

EP   0 008 203   8/1982

(Continued)

OTHER PUBLICATIONS

Guillory (in Brittain et al.), "Polymorphism in ,etc.," NY:Marcel Dekker, Inc. 1999, 183-226.*

(Continued)

Primary Examiner—Patricia L. Morris
(74) Attorney, Agent, or Firm—Kathryn L. Sieburth; Mary E. McCarthy; Charles M. Kinzig

(57) ABSTRACT

A process for preparing a compound of formula (I):

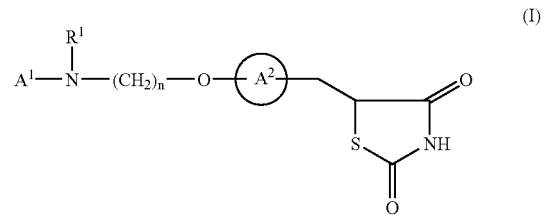

or a tautomeric form thereof or a pharmaceutically acceptable salt thereof, or a pharmaceutically acceptable solvate thereof, wherein:
$A^1$ represents a substituted or unsubstituted aromatic heterocyclyl group;
$R^1$ represents a hydrogen atom, an alkyl group, an acyl group, an aralkyl group, wherein the aryl moiety may be substituted or unsubstituted, or a substituted or unsubstituted aryl group;
$A^2$ represents a benzene ring having in total up to five substituents; and
n represents an integer in the range of from 2 to 6, which process comprises catalytically reducing a compound of formula (II):

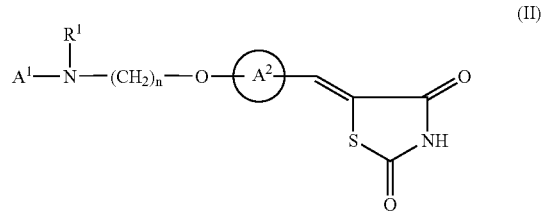

wherein $A^1$, $R^1$, $A^2$ and n are as defined in relation to formula (I), characterised in that the reduction reaction is carried out using a hydrogen pressure above 20 psi; and thereafter if required forming a pharmaceutically acceptable salt and/or a pharmaceutically acceptable solvate of the compound of formula (I).

16 Claims, No Drawings

U.S. PATENT DOCUMENTS

| | | |
|---|---|---|
| 6,686,475 B2 | 2/2004 | Hindley |
| 7,091,359 B2 * | 8/2006 | Giles et al. .............. 548/183 |
| 2002/0042519 A1 | 4/2002 | Giles et al. |
| 2002/0049240 A1 | 4/2002 | Hindley et al. |
| 2002/0050563 A1 | 5/2002 | Hindley et al. |
| 2002/0106762 A1 | 8/2002 | Hindley et al. |

FOREIGN PATENT DOCUMENTS

| | | |
|---|---|---|
| EP | 0 257 781 | 7/1987 |
| EP | 0 306 228 | 3/1989 |
| WO | WO 92/07838 | 5/1992 |
| WO | WO 92/07839 | 5/1992 |
| WO | WO 93/10254 | 5/1993 |
| WO | WO 93/13095 | 7/1993 |
| WO | WO 94/05659 | 3/1994 |
| WO | WO 98/37073 | 8/1998 |
| WO | WO 99/23095 | 5/1999 |

OTHER PUBLICATIONS

Vippagunta et al., "Crystalline solids", Advanced Drug Delivery Reviews 48 (2001) 3-26.*

House. Modern Synthetic Reactions, 2nd Ed., pp. 1-8 (1972).

Teruo et al., "Preparation of Thiazolidine-2,4-diones as Aldose Reductase Inhibitors". *Chem. Abstracts*, 115(17): Oct. 28, 1991. XP-002066776.

Augustine, Robert L., (1965). Catalytic Hydrogenation *Techniques and Application in Organinc Syntheses*. Chapter 3 Catalysts and Conditions (pp. 23-56). New York: Marcel Dekker, Inc.

* cited by examiner

PROCESS FOR THE PREPARATION OF THIAZOLIDINEDIONE DERIVATIVES

This application is a continuation of U.S. application Ser. No. 11/326,003 filed Jan. 5, 2006, now abandoned, which is a divisional of U.S. application Ser. No. 10/288,072, filed Nov. 4, 2002, now U.S. Pat. No. 7,091,359, which is a continuation of U.S. application Ser. No. 10/082,995, filed Feb. 26, 2002, now abandoned, which is a continuation of U.S. application Ser. No. 09/530,888, filed Jul. 10, 2000, now abandoned, which is a 371 of International Application No. PCT/EP98/06997, filed Oct. 27, 1998.

This invention relates to a novel process and in particular to a process for preparing certain substituted thiazolidinedione derivatives.

European Patent Application, Publication Number 0306228 discloses certain thiazolidinedione derivatives of formula (A):

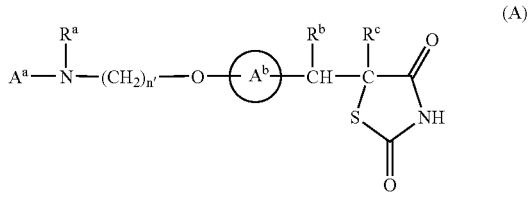

(A)

or a tautomeric form thereof or a pharmaceutically acceptable salt thereof, or a pharmaceutically acceptable solvate thereof, wherein:

$A^a$ represents a substituted or unsubstituted aromatic heterocyclyl group;

$R^a$ represents a hydrogen atom, an alkyl group, an acyl group, an aralkyl group, wherein the aryl moiety may be substituted or unsubstituted, or a substituted or unsubstituted aryl group;

$R^b$ and $R^c$ each represent hydrogen or $R^b$ and $R^c$ together represent a bond;

$A^b$ represents a benzene ring having in total up to five substituents; and n' represents an integer in the range of from 2 to 6.

EP 0306228 also discloses a process for reducing the compounds of formula (A) wherein $R^b$ and $R^c$ together represent a bond (the 'benzylidene thiazolidine-2, 4-diones') to the corresponding compounds of formula (A) wherein $R^b$ and $R^c$ each represent hydrogen (the 'benzylthiazolidine-2, 4-diones'). The particular reduction methods disclosed in EP 0306228 are dissolving metal methods and catalytic hydrogenation methods.

It has now been discovered that when the catalytic hydrogenation of the benzylidene thiazolidine-2, 4-diones is carried out using an elevated pressure of hydrogen that the reaction can be effected with a surprising reduction in the catalytic loading and reaction time and, most surprisingly, produces a significant reduction in by-product formation.

Accordingly, the present invention provides a process for preparing a compound of formula (I):

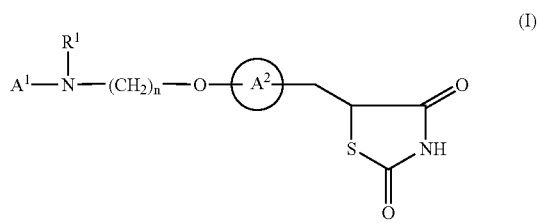

(I)

or a tautomeric form thereof or a pharmaceutically acceptable salt thereof, or a pharmaceutically acceptable solvate thereof, wherein:

$A^1$ represents a substituted or unsubstituted aromatic heterocyclyl group;

$R^1$ represents a hydrogen atom, an alkyl group, an acyl group, an aralkyl group, wherein the aryl moiety may be substituted or unsubstituted, or a substituted or unsubstituted aryl group;

$A^2$ represents a benzene ring having in total up to five substituents; and n represents an integer in the range of from 2 to 6, which process comprises catalytically reducing a compound of formula (II):

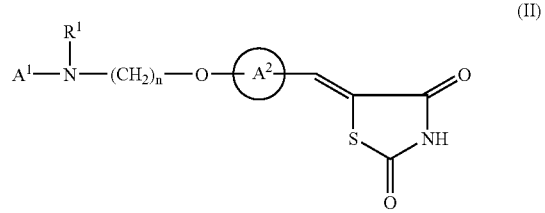

(II)

wherein $A^1$, $R^1$, $A^2$ and n are as defined in relation to formula (I), characterised in that the reduction reaction is carried out using a hydrogen pressure above 20 psi, and thereafter, if required, forming a pharmaceutically acceptable salt and/or a pharmaceutically acceptable solvate of the compound of formula (I).

Suitably the reaction is carried out at a pressure in the range of from 50 to 1500 psi, such as 60 to 1500 psi, 75 to 1500 psi, 200 to 1500 psi, 70 to 1000 psi or 200 to 1000 psi, suitably 70 to 1000psi.

Examples of reaction pressures include 70, 75, 80, 500 and 1000 psi.

A suitable hydrogenation catalyst is a noble metal catalyst, suitably a palladium catalyst.

Favoured catalysts are supported noble metal catalysts, such as a palladium-on-carbon catalyst, typically comprising 5% to 10% of palladium.

A preferred catalyst is a 10% palladium-on-carbon catalyst.

Catalyst loadings (expressed as w/w % of catalyst to substrate) in the reaction are typically in the range of from 5 to 100%, usually 10 to 50% and preferably 25 to 50%.

The reaction may be carried out using any suitable solvent such as acetic acid, or an alkanol, such as methanol or ethanol, preferably admixed with an aqueous mineral acid such as hydrochloric acid; or tetrahydrofuran, preferably admixed with an aqueous mineral acid such as hydrochloric acid. Preferably the solvent is acetic acid or aqueous acetic acid, for example a 1:2 acetic acid:water mixture.

The reaction is carried out at a temperature which provides a suitable rate of formation of the required product, suitably at an elevated temperature, preferably above 70° C., for example in the range of from 80° C. to 115° C.

The compounds of formula (I) are isolated from the reaction and subsequently purified by use of conventional isolation and purification methods such as chromatography and crystallization/recrystalliazation.

The suitable, apt, favoured and preferred values of the variables $A^1$, $A^2$, $R^1$ and n in formulae (I) and (II) are as defined in relation to formula (I) of EP 0306228.

A most preferred value of $A^1$ is a 2-pyridyl group.

A most preferred value of $A^2$ is a moiety of formula:

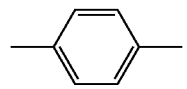

A most preferred value of $R^1$ is a methyl group.

A most preferred value of n is 2.

A most preferred value of formula (I) is 5-{4-[2-(N-methyl-N-(2-pyridyl)amino)ethoxy]benzyl}-2,4-thiazolidinedione, or a tautomeric form thereof or a salt thereof, or a solvate thereof.

Crystalline 5-{4-[2-(N-methyl-N-(2-pyridyl)amino)ethoxy]benzylidene}-2,4-thiazolidinedione is isolated from the present reaction and as such forms a further aspect of the present invention. A suitable crystallization/recrystallization solvent is denatured ethanol, the crystallization is favourably effected from refluxing solvent which is allowed to cool to provide the required compound.

A most preferred value of formula (II) is 5-{4-[2-(N-methyl-N-(2-pyridyl)amino)ethoxy]benzylidene}-2,4-thiazolidinedione or a tautomeric form thereof or a salt thereof, or a solvate thereof.

Suitable salts are pharmaceutically acceptable salts.

Suitable pharmaceutically acceptable salts include metal salts, such as for example aluminium, alkali metal salts such as sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-b-phenethylamine, dehydroabietylamine, N,N'-bisdehydroabietylamine, glucamine, N-methylglucamine or bases of the pyridine type such as pyridine, collidine or quinoline.

In addition should be mentioned those pharmaceutically acceptable salts provided by pharmaceutically acceptable acids including mineral acids, including salts provided by mineral acids, such as hydrobromic, hydrochloric and sulphuric acids, and organic acids, such as methanesulphonic, tartaric and maleic acids, especially tartaric and maleic acid. A preferred salt is a maleate salt.

Suitable solvates are pharmaceutically acceptable solvates, such as hydrates.

The compounds of formula (II) are prepared according to known methods, for example by use of the appropriate method disclosed in EP 0306228. The contents of EP 0306228 are incorporated herein by reference.

The following example illustrates the invention but does not limit it in any way.

EXAMPLE

Reduction of (Z)-5-{4-[2-(N-methyl-N-(2-pyridyl)amino)ethoxy]benzylidene}-2,4-thiazolidinedione to 5-{4-[2-(N-methyl-N-(2-pyridyl)amino)ethoxy]benzyl}-2,4-thiazolidinedione To a solution of (Z)-5-{[4-[2-(N-methyl-N-(2-pyridyl)amino)ethoxy]benzylidene}-2,4-thiazolidinedione (123 kg) in glacial acetic acid (1232 L) is added 10% palladium on charcoal (Johnson-Matthey type 87 L, 123 kg, catalyst contains ~50% w/w water and hence the catalyst loading was 50% w/w). The resulting mixture is hydrogenated at 70-80 p.s.i. hydrogen pressure at about 95° C. After the starting material is consumed (15-20 hours), the reaction mixture is cooled to about 65° C. and the catalyst is removed by filtration. The resulting solution is concentrated under reduced pressure to low volume and the residue is dissolved in denatured ethanol (500 L) at 60° C. The solution is heated to reflux and then cooled to ambient temperature to effect crystallisation. The product, 5-{[4-[2-(N-methyl-N-(2-pyridyl)amino)ethoxy]benzyl}-2,4-thiazolidinedione, is isolated by filtration, and dried in vacuo at 45° C. Typical yields are 70-80%.

Effect of Change of Reaction Pressure

The above reaction can be performed over a range of pressures resulting in a significant reduction in reaction time and catalyst loading, as shown below.

| Reaction number | Conditions | Reaction Time (hours.) |
| --- | --- | --- |
| 1 | (75 psi, 100% catalyst) | 15-20 |
| 2 | 1000 psi, 100% catalyst | <2 |
| 3 | 1000 psi, 50% catalyst | 7 |
| 4 | 500 psi, 100% catalyst | 4 |
| 5 | 500 psi, 50% catalyst | ca.12 |

The invention claimed is:

1. A process for preparing a compound selected from 5-{4-[2-(N-methyl-N-(2-pyridyl)amino)ethoxy]benzyl}-2,4-thiazolidinedione, or a tautomeric form thereof, or a pharmaceutical acceptable salt thereof or a hydrate thereof, comprising catalytically reducing 5-{4-[2-(N-methyl-N-(2-pyridyl)amino)ethoxy]benzylidene}-2,4-thiazolidinedione, or a tautomeric form thereof, or a salt thereof, or a hydrate thereof, at a temperature above 70° C. using a hydrogen pressure above 20 psi, and thereafter optionally forming a pharmaceutically acceptable salt or a hydrate of 5-{4-[2-(N-methyl-N-(2-pyridyl)amino)ethoxy]benzyl}-2,4-thiazolidinedione, or a tautomeric form thereof.

2. The process according to claim 1, wherein the hydrogen pressure is in the range of from 50 to 1500 psi.

3. The process according to claim 1, wherein the hydrogen pressure is in the range of from 70 to 1000 psi.

4. The process according to claim 1, wherein the hydrogen pressure is in the range of from 70 to 80 psi.

5. The process according to claim 1, wherein the catalyst is a palladium catalyst.

6. The process according to claim 5, wherein the catalyst comprises a palladium-on-carbon catalyst.

7. The process according to claim 5, wherein the catalyst comprises a 5-10% palladium-on-carbon catalyst.

8. The process according to claim 5, wherein the catalyst loading is 10 to 50 wt/wt %.

9. The process according to claim 5, wherein the catalyst loading is 25 to 50 wt/wt %.

10. The process according to claim 1, wherein the reduction is conducted at a temperature in the range of from 800 to 115° C.

11. The process according to claim 1, wherein 5-{4-[2-(N-methyl-N-(2-pyridyl)amino)ethoxy]benzylidene}-2,4-thiazolidinedione, or a tautomeric form thereof is catalytically reduced.

12. The process according to claim 1, wherein a salt of 5-{4-[2-(N-methyl-N-(2-pyridyl)amino)ethoxy]benzylidene}-2,4-thiazolidinedione, or a tautomeric form thereof is catalytically reduced.

13. The process according to claim 12, wherein a mineral acid salt of 5-{4-[2-(N-methyl-N-(2-pyridyl)amino)ethoxy]benzylidene}-2,4-thiazolidinedione, or a tautomeric form thereof is catalytically reduced.

14. The process according to claim 13, wherein the mineral acid is hydrobromic acid, hydrochloric acid, or sulphuric acid.

15. The process according to claim 12, wherein an organic acid salt of 5-{4-[2-(N-methyl-N-(2-pyridyl)amino)ethoxy]benzylidene}-2,4-thiazolidinedione, or a tautomeric form thereof is catalytically reduced.

16. The process according to claim 15, wherein the organic acid is methanesulphonic acid or tartaric acid.

* * * * *